United States Patent [19]

Thottathil et al.

[11] Patent Number: 4,602,092

[45] Date of Patent: Jul. 22, 1986

[54] METHOD FOR MAKING PHOSPHINIC ACID INTERMEDIATES

[75] Inventors: John K. Thottathil, Trenton; Jerome L. Moniot, Chester, both of N.J.

[73] Assignee: E. R. Squibb & Sons, Inc., Princeton, N.J.

[21] Appl. No.: 693,418

[22] Filed: Jan. 22, 1985

Related U.S. Application Data

[63] Continuation-in-part of Ser. No. 533,485, Sep. 19, 1983, abandoned.

[51] Int. Cl.⁴ .............................................. C07F 9/32
[52] U.S. Cl. .................................. 548/112; 558/136; 558/307; 548/113; 560/105; 260/502.4 R; 260/502.5 D
[58] Field of Search ......... 260/970, 502.4 R, 502.5 D, 260/465 R; 546/22, 23; 548/112, 113; 560/105

[56] References Cited

U.S. PATENT DOCUMENTS

| | | | |
|---|---|---|---|
| 4,168,267 | 9/1979 | Petrillo, Jr. .................. | 260/936 |
| 4,316,905 | 2/1982 | Krapcho ........................ | 424/251 |
| 4,316,906 | 2/1982 | Ondetti et al. ................ | 424/251 |
| 4,337,201 | 6/1982 | Petrillo ........................ | 424/251 |

OTHER PUBLICATIONS

Thottathil et al., "Tetrahedron Letters", vol. 25, No. 42, pp. 4737–4740, (1984).

*Primary Examiner*—Anton H. Sutto
*Attorney, Agent, or Firm*—Lawrence S. Levinson; Burton Rodney

[57] ABSTRACT

A method is provided for preparing phosphinic acid prodrug intermediates which are useful in preparing phosphinic acid angiotensin-converting enzyme inhibitors which method includes the step of coupling a phosphonous acid or its ester of the structure

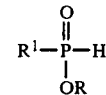

wherein R is H or lower alkyl and $R^1$ is lower alkyl, aryl, arylalkyl, cycloalkyl or cycloalkylalkyl, with an alkylating agent of the structure

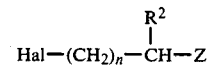

wherein Hal is Cl, Br or I, n is 0 or 1, $R^2$ is H or lower alkyl, and Z is H, lower alkyl, $-CO_2R^3$ (wherein $R^3$ is H or lower alkyl),

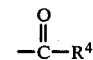

(wherein $R^4$ is H, lower alkyl, aryl or arylalkyl), $-CN$, or

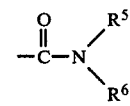

(wherein $R^5$ and $R^6$ may be the same or different and are selected from the group consisting of H, lower alkyl, aryl, aryl-lower alkyl, cycloalkyl or cycloalkylalkyl and at least one of $R^5$ and $R^6$ is other than H, or $R^5$ and $R^6$ can be taken with the N-atom to form a 5-, 6- or 7-membered heterocyclic ring which 5-, 6- or 7-membered N-containing ring may or may not contain a $CO_2R^3$ group and which 5- or 6-membered N-containing ring may or may not be fused to an aryl ring), in the presence of a silylating agent, to form the phosphinic acid intermediate of the structure

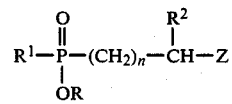

wherein R, $R^1$, $R^2$, n and Z are as defined above.

17 Claims, No Drawings

METHOD FOR MAKING PHOSPHINIC ACID INTERMEDIATES

REFERENCE TO OTHER APPLICATIONS

This application is a continuation-in-part of application Ser. No. 533,485, filed Sept. 19, 1983, now abandoned.

FIELD OF THE INVENTION

The present invention relates to a method for preparing phosphinic acid intermediates having the structure $$R^1 - \underset{\underset{OR}{|}}{\overset{\overset{O}{\|}}{P}} - (CH_2)_n - \underset{\underset{}{|}}{\overset{R^2}{\underset{}{C}H}} - Z \qquad I$$

wherein

R is H or lower alkyl;

$R^1$ is lower alkyl, aryl, arylalkyl, cycloalkyl, or cycloalkylalkyl; $R^2$ is H or lower alkyl; Z is H, lower alkyl, $-CO_2R^3$ (wherein $R^3$ is H or lower alkyl), $$-\overset{\overset{O}{\|}}{C} - R^4$$

(wherein $R^4$ is H, lower alkyl, aryl or arylalkyl), $-CN$, or $$-\overset{\overset{O}{\|}}{C} - N\overset{R^5}{\underset{R^6}{\diagdown}}$$

(wherein $R^5$ and $R^6$ are the same or different and can be hydrogen, lower alkyl, aryl, aryl-lower alkyl, cycloalkyl or cycloalkylalkyl, and at least one of $R^5$ and $R^6$ is other than hydrogen, or $R^5$ and $R^6$ can be taken together with the nitrogen atom to form a 5-, 6- or 7-membered heterocyclic ring, $$-N\bigcirc \quad ,$$

which ring may or may not include a carboxyl substituent $-CO_2R^3$, and which nitrogen containing ring containing 5 or 6 members may or may not include a fused aryl ring, such as a phenyl ring, so that the nitrogen containing ring $$-N\bigcirc$$

together with its fused aryl ring may form indole or tetrahydro-isoquinoline systems such as

[structures with $-N$ and $(CO_2R^3)_{n'}$]

where in the above formulae n' is 0 or 1) and n is 0 or 1, which intermediates are useful in the preparation of phosphonic acid angiotensin-converting enzyme inhibitors such as described in U.S. Pat. Nos. 4,168,267 and 4,337,201.

BRIEF DESCRIPTION OF THE INVENTION

The method of the present invention for making phosphinic acid intermediates of formula I includes the step of reacting a phosphonous acid or ester of the structure $$R^1 - \underset{\underset{OR}{|}}{\overset{\overset{O}{\|}}{P}} - H \qquad II$$

wherein R is H or lower alkyl and $R^1$ is lower alkyl, aryl, arylalkyl, cycloalkyl or cycloalkylalkyl, with an alkylating agent of the structure $$Y - (CH_2)_n - \overset{\overset{R^2}{|}}{C}H - Z \qquad III$$

wherein Y is a leaving group such as halogen including Cl, Br or F, mesyloxy or toxyloxy n is 0 or 1, $R^2$ is H or lower alkyl, and Z is H, lower alkyl, $CO_2R^3$ (wherein $R^3$ is H or lower alkyl), $$-\overset{\overset{O}{\|}}{C} - R^4$$

wherein $R^4$ is H, lower alkyl, aryl or arylalkyl), CN, or $$-\overset{\overset{O}{\|}}{C} - N\overset{R^5}{\underset{R^6}{\diagdown}}$$

(wherein $R^5$ and $R^6$ are the same or different and can be hydrogen, lower alkyl, aryl, aryl-lower alkyl, cycloalkyl or cycloalkylalkyl, and at least one of $R^5$ and $R^6$ is other than hydrogen, or $R^5$ and $R^6$ can be taken together with the nitrogen atom to form a 5-, 6- or 7-membered heterocyclic ring

which ring may or may not include a carboxyl group $CO_2R^3$, and which 5- or 6-membered N-containing ring may or may not include a fused aryl ring, such as a phenyl ring, which fused systems are exemplified above), in the presence of a silylating agent and an inert organic solvent to form the phosphinic acid intermediate I which may be separated from the reaction mixture and used in the preparation of phosphinic acid angiotensin-converting enzyme inhibitors such as described in U.S. Pat. Nos. 4,168,267 and 4,337,201.

It is believed that the process as described above proceeds according to the following reaction sequences.

A. Where R is H

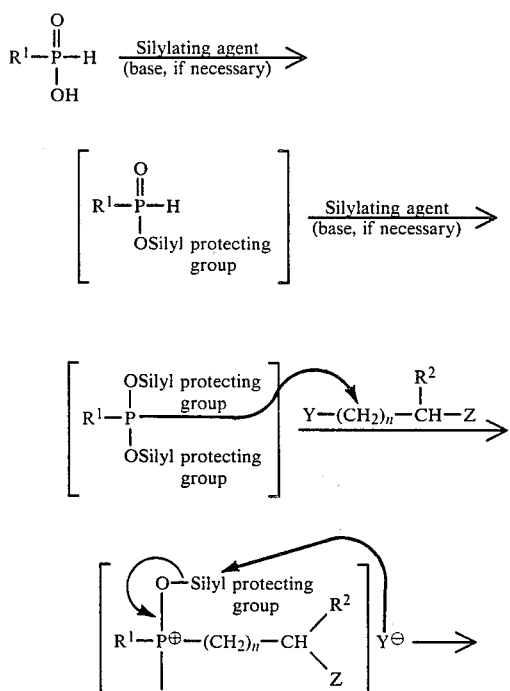

B. Where R is alkyl

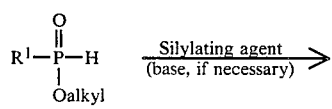

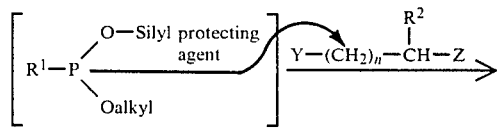

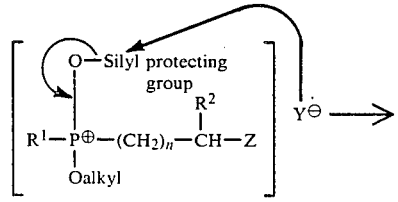

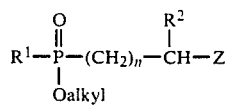

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl" or "lower alkyl" as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy" or "alkylthio", as used throughout the specification either by itself or as part of a larger group, refers to groups having 1 to 8 carbon atoms. Alkoxy or alkylthio groups having 1 to 3 carbon atoms are preferred.

The term "arylalkyl" or "cycloalkylalkyl", as used throughout the specification either by itself or as part of a larger group, refers to an "alkyl" group as defined above containing an "aryl" or "cycloalkyl" substituent.

The term "alkanoyl" as used throughout the specification either by itself or as part of a larger group, refers to an "alkyl" group as defined above linked to a carbonyl

group.

DETAILED DESCRIPTION OF THE INVENTION

In carrying out the method of the invention to prepare compounds of formula I, the phosphonous acid or ester starting material II will be reacted with the alkylating agent in the presence of the silylating agent employing mild conditions, namely, a temperature of within the range of from about $-10°$ C. to about reflux temperature (about 120° C.), and preferably from about 0° C. to about 50° C. The reaction will be carried out for a period ranging from about 2 to about 10 hours and preferably from about 5 to about 8 hours in the presence of an inert organic solvent such as chloroform, acetonitrile, dichloromethane, ethyl ether, tetrahydrofuran or dioxane, and optionally, in the presence of an organic base, such as triethylamine, pyridine or N,N-dimethylamine.

Examples of phosphonous acids or esters II useful as starting materials in carrying out the present invention include, but are not limited to,

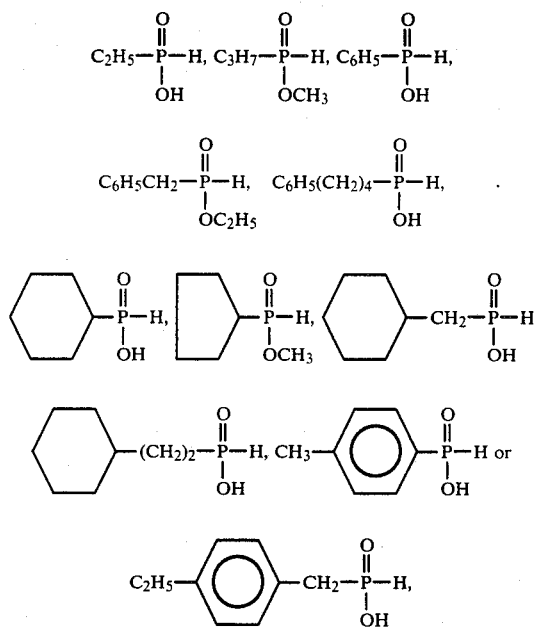

with

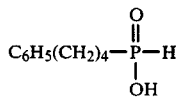

or esters thereof being preferred.

Examples of alkylating agents III useful in carrying out the present invention include, but are not limited to,

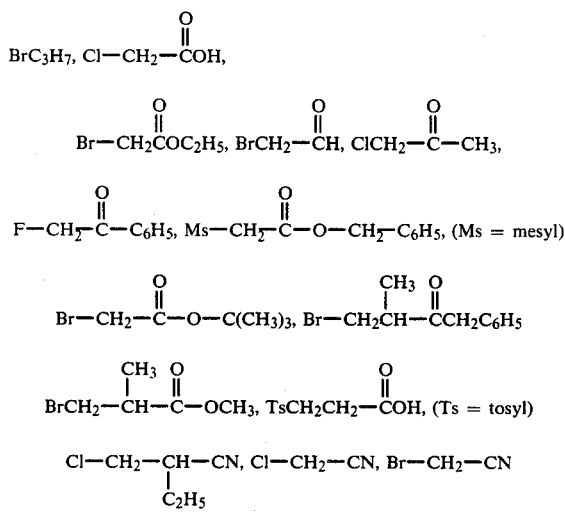

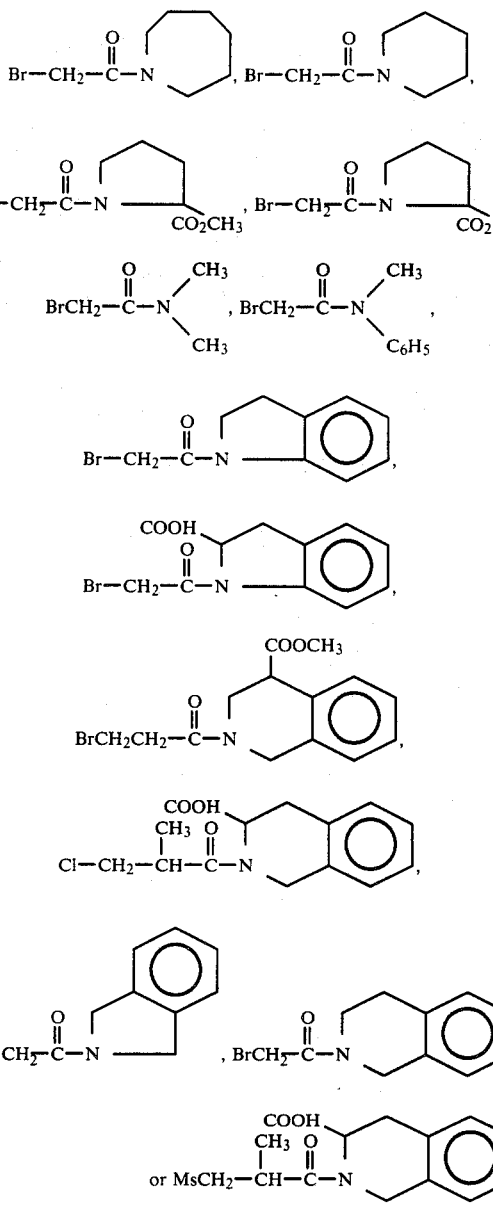

with

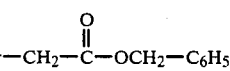

being preferred.

Examples of silylating agents suitable for use in carrying out the method of the present invention include, but are not limited to, trimethylsilyl chloride and triethylamine, monosilylacetamide, bissilylacetamide, monosilyltrifluoroacetamdie and bissilyltrifluoroacetamide.

Generally, the phosphonous acid or ester II may be employed in a molar ratio to the alkylating agent III of within the range of from about 0.5:1 to about 10:1 and the phosphonous acid or ester II may be employed in a molar ratio to the silylating agent of within the range of from about 0.06:1 to about 2:1. However, usually, in carrying out the method of the invention as described above the amount of phosphonous acid or ester II employed vis-a-vis the alkylating agent III and the silylating agent will depend upon the R substituents in the starting phosphonous acid or ester II and the Z substituent in the alkylating agent III. Thus, where R is lower alkyl and Z is CO$_2$ alkyl, lower alkyl,

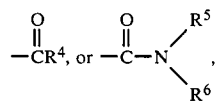

then the phosphonous acid or ester II will be employed in a molar ratio to the alkylating agent III of within the range of from about 0.5:1 to about 10:1, preferably from about 0.75:1 to about 1.25:1, and the phosphonous acid of ester II will be employed in a molar ratio to the silylating agent of within the range of from about 0.1:1 to about 2:1, and preferably from about 0.75:1 to about 1.25:1.

Where in the phosphonous acid or ester II, R is H and in the alkylating agent III, Z is lower alkyl, CO$_2$R$^3$ (wherein R$^3$ is lower alkyl),

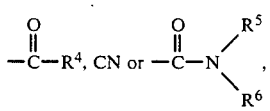

the phosphonous acid or ester II will be employed in a molar ratio to the alkylating agent III of within the range of from about 0.5:1 to about 10:1, preferably from about 0.75:1 to about 1.25:1, and the phosphonous acid or ester II will be employed in a molar ratio to the silylating agent of within the range of from about 0.1:1 to about 1:1, and preferably from about 0.3:1 to about 0.7:1.

Where a phosphonous acid starting material is used, that is in formula II, R is H, and in the alkylating agent III, Z is CO$_2$H or

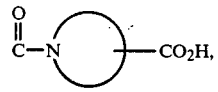

then the phosphonous acid II will be employed in a molar ratio to the alkylating agent III of within the range of from about 0.5:1 to about 10:1, preferably from about 0.75:1 to about 1.25:1, and the phosphonous acid II will be employed in a molar ratio to the silylating agent of within the range of from about 0.06:1 to about 0.5:1, and preferably from about 0.2:1 to about 0.4:1.

Where a phosphonous acid ester of formula II (that is, R is alkyl) is employed and the alkylating agent used is an acid, that is in formula III, Z is CO$_2$H or

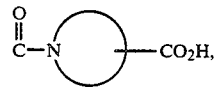

then the phosphonous acid ester II will be employed in a molar ratio to the alkylating agent of within the range of from about 0.5:1 to about 10:1, preferably from about 0.75:1 to about 1.25:1, and the phosphonous acid ester II employed in a molar ratio to the silylating agent of within the range of from about 0.06:1 to about 1:1, and preferably from about 0.3:1 to about 0.7:1.

Where the phosphinic acid intermediate I is obtained in the form of an ester, such ester may be converted to the free acid by conventional means such as by reacting the ester with sodium hydroxide.

The esters of formula I where R is lower alkyl can be obtained from the phosphinic acid compounds, that is wherein R is H, by conventional esterification means, for example, by esterification with diazomethane or by reaction with methyl iodide (or other alkyl halide) and a base, such as triethylamine, potassium carbonate and the like.

The following Examples represent preferred embodiments of the present invention. Unless otherwise indicated, temperatures are expressed in degrees Centigrade.

EXAMPLE 1

[Hydroxy-(4-phenylbutyl)phosphinyl]acetic acid, phenylmethyl ester

To a solution of 4-phenylbutyl phosphonous acid (2.0 g, 0.01 mole) in chloroform (40 ml) was added triethylamine (3.2 ml, 0.022 mole) and cooled in an ice bath to 0° C. Trimethyl silyl chloride (2.8 ml, 0.022 mole) was added to the above solution dropwise, followed by benzyl bromoacetate (1.6 ml, 0.011 mole). The ice bath was removed and the mixture stirred at room temperture for 5 hours and poured into 10% aqueous HCl (30 ml) and crushed ice (20 g). After shaking the mixture in a separatory funnel, the chloroform layer was separated and the aqueous layer extracted with dichloromethane (2×50 ml). The combined organic phase was washed with brine, dried over anhydrous sodium sulfate and the solvents removed on a rotavap. The resulting crude thick oil (3.5 g) was dissolved in 30 ml ether; hexane was added dropwise to get a turbid solution and left at room temperature overnight to complete the crystallization. The resulting product was cooled in the freezer for 2 hours, filtered and the solid was washed very thoroughly with hexane (50 ml), ether (50 ml) and again very thoroughly with hexane (50 ml), ether (50 ml) in that order. The solid was vacuum dried to get 2.48 g (71%) of title compound, m.p. 68°–70° C. TLC: Silica gel, CH$_2$Cl$_2$:MeOH:HOAc (20:1:1) shows a single spot at R$_f$=0.25.

EXAMPLE 2

[Hydroxy(4-phenylbutyl)phosphinyl]acetic acid, ethyl ester

Following the procedure of Example 1, except substituting ethylbromoacetate for benzyl bromoacetate, the title compound is obtained.

EXAMPLE 3

[Hydroxy(4-phenylbutyl)phosphinyl]acetic acid, methyl ester

Following the procedure of Example 1, except substituting methyl bromoacetate for benzyl bromoacetate, the title compound is obtained.

EXAMPLE 4

[Hydroxy(4-phenylbutyl)phosphinyl]acetic acid, propyl ester

Following the procedure of Example 1, except substituting propylbromoacetic acid for benzyl bromoacetate, the title compound is obtained.

EXAMPLE 5

[Hydroxy(ethyl)phosphinyl]acetic acid

Following the procedure as set out in Example 1, except substituting ethylphosphonous acid for 4-phenylbutylphosphonous acid, and substituting chloroacetic acid for benzylbromoacetate, the title compound is obtained.

EXAMPLE 6

[Hydroxy(cyclohexyl)phosphinyl]acetic acid, ethyl ester

Following the procedure as set out in Example 1, except substituting cyclohexylphosphonous acid for 4-phenylbutylphosphonous acid, and substituting ethylchloroacetate for benzylbromoacetate, the title compound is obtained.

EXAMPLE 7

[Hydroxy(phenyl)phosphinyl]acid, phenylethyl ester

Following the procedure as set out in Example 1, except substituting phenylphosphonous acid for 4-phenylbutylphosphonous acid, and substituting phenylethylchloroacetate for benzylbromoacetate, the title compound is obtained.

EXAMPLE 8

[Hydroxy(cyclohexylmethyl)phosphinyl]propionic acid

Following the procedure as set out in Example 1, except substituting cyclohexylmethylphosphonous acid for 4-phenylbutylphosphonous acid, and substituting bromopropionic acid for benzylbromoacetate, the title compound is obtained.

EXAMPLE 9

(4-Phenylbutyl)methylphosphonic acid

Following the procedure as set out in Example 1, except substituting bromomethane for benzylbromoacetate, the title compound is obtained.

EXAMPLE 10

[Hydroxy(propyl)phosphinyl]-2-methyl propionyl nitrile

Following the procedure as set out in Example 1, except substituting propylphosphonous acid for 4-phenylbutylphosphonous acid, and substituting 3-bromo-2-methylpropionolnitrile for benzylbromoacetate, the title compound is obtained.

EXAMPLE 11

[Hydroxy(4-phenylbutyl)phosphinyl]propionyl methyl ketone

Following the procedure as set out in Example 1, except substituting 2-bromoethyl(methyl)ketone for benzylbromoacetate, the title compound is obtained.

EXAMPLE 12

[Hydroxy(phenyl)phosphinyl]propional aldehyde

Following the procedure as set out in Example 1, except substituting phenylphosphonous acid for 4-phenylbutylphosphonous acid, and substituting 2-bromopropional aldehyde for benzylbromoacetate, the title compound is obtained.

EXAMPLE 13

[Hydroxy(4-phenylbutyl)phosphinyl]propionic acid

Following the procedure as set out in Example 1, except substituting 2-bromopropionic acid for benzylbromoacetate, the title compound is obtained.

EXAMPLE 14

[Hydroxy-(4-phenylbutyl)]phosphinyl]acetyl-L-proline

Following the procedure of Example 1 except substituting bromoacetyl-L-proline for benzylbromoacetate, the title compound is obtained.

EXAMPLE 15

[Hydroxy-(4-phenylbutyl)]phosphinyl]-N,N-dimethylacetamide

Following the procedure of Example 1 except substituting N,N-dimethylbromoacetamide for benzylbromoacetate, the title compound is obtained.

EXAMPLE 16

[Hydroxy(4-phenylbutyl)phosphinyl]-1-methylpropionic acid

Following the procedure of Example 1, except substituting 2-bromo-1-methylpropionic acid for benzylbromoacetate, the title compound is obtained.

EXAMPLE 17

1-[Hydroxy-(4-phenylbutyl)phosphinyl]acetyl indoline

Following the procedure of Example 1 except substituting N-bromoacetyl indoline for benzylbromoacetate, the title compound is obtained.

EXAMPLE 18

1-[2-[Hydroxy-(4-phenybutyl)phosphinyl]propionyl]indoline-2-carboxylic acid

Following the procedure of Example 1 except substituting 1-(2-bromopropionyl)indoline-2-carboxylic acid for benzylbromoacetate, the title compound is obtained.

EXAMPLE 19

2-[2-[Hydroxy-(4-phenylbutyl)phosphiny]-1-methylpropionyl]-1,2,3,4-tetrahydro isoquinoline Following the procedure of Example 1 except substituting 2-[2-bromo-1-methylpropionyl]-1,2,3,4-tetrahydro isoquinoline for benzylbromoacetate, the title compound is obtained.

EXAMPLE 20

2-[Hydroxy-(4-phenylbutyl)phosphinyl]acetyl-1,2,3,4-tetrahydro isoquinoline-1-carboxylic acid Following the procedure of Example 1 except substituting 2-bromoacetyl-1,2,3,4-tetrahydro isoquinoline-1-carboxylic acid for benzylbromoacetate, the title compound is obtained.

EXAMPLE 21

[Ethoxy-(4-phenylbutyl)phosphinyl]acetic acid

To a solution of 4-phenylbutyl phosphonous acid, ethyl ether (0.5 g, 0.0022 mole) in chloroform (10 ml) was added triethylamine (0.68 ml, 0.0048 mole) and the solution was cooled in an ice bath to 0° C. Trimethyl silyl chloride (0.6 ml, 0.0048 mole) was added to the above solution dropwise, followed by bromoacetic acid (0.34 g, 0.0024 mole). The ice bath was removed and the mixture stirred at room temperature for 5 hours and poured into 10% aqueous HCl (30 ml) and crushed ice (20 g). After shaking the mixture in a separatory funnel, the chloroform layer was separated and the aqueous layer extracted with dichloromethane (2×50 ml). The combined organic phase was washed with brine, dried over anhydrous sodium sulfate and the solvents removed on a rotavap. The resulting crude thick oil was vacuum dried to get 0.61 g (97%) of title compound in the form of an oil, TLC: Silica gel, $CH_2Cl_2$:MeOH:-HOAc shows one main spot at $R_f=0.37$.

EXAMPLE 22

[Hydroxy-(4-phenylbutyl)phosphinyl]acetic acid, ethyl ester

To a solution of 4-phenylbutyl phosphonous acid (1.0 g, 0.005 mole) in chloroform (20 ml) was added triethylamine (1.6 ml, 0.011 mole) and the solution was cooled in an ice bath to 0° C. Trimethyl silyl chloride (1.4 ml, 0.011 mole) was added to the above solution dropwise, followed by ethyl bromoacetate (0.84 g, 0.56 ml, 0.011 mole). The ice bath was removed and the mixture stirred at room temperature overnight. The mixture was poured into 10% aqueous HCl (10 ml) and crushed ice HCl (10 ml) and crushed ice (10 g). After shaking the mixture in a separatory funnel, the chloroform layer was separated and the aqueous layer extracted with dichloromethane (2×50 ml). The combined organic phase was washed with brine, dried over anhydrous sodium sulfate and the solvents removed on a rotavap. The resulting crude thick oil (1.42 g) was vacuum dried to get 1.42 g (99%) of title compound in the form of an oil. TLC: silica gel, $CH_2Cl_2$:MeOH:HOAc shows one main spot, but elongated, $R_f=0.29$.

EXAMPLE 23

[Hydroxy-(4-phenylbutyl)phosphinyl]acetic acid

To a solution of 4-phenylbutyl phosphonous acid (0.5 g, 0.002525 mole) in chloroform (10 ml) was added triethylamine (1.16 ml, 0.00833 mole) and the solution was cooled in an ice bath to 0° C. Trimethyl silyl chloride (1.06 ml, 0.00833 mole) was added to the above solution dropwise, followed by bromoacetic acid (0.36 g, 0.00277 mole). The ice bath was removed and the mixture stirred at room temperature for 3 hours and poured into 10% aqueous HCl (30 ml) and crushed ice (20 g). After shaking the mixture in a separatory funnel, the chloroform layer was separated and the aqueous layer extracted with dichloromethane (2×50 ml). The combined organic phase was washed with brine, dried over anhydrous sodium sulfate and the solvents removed on a rotavap. The resulting crude thick oil (0.6 g) was dissolved in 30 ml ether; hexane was added dropwise to get a turbid solution and left at room temperature overnight to complete the crystallization. The resulting product was cooled in the freezer for 12 hours, filtered and the solid was washed very thoroughly with hexane (50 ml), ether (50 ml) and again very thoroughly with hexane (50 ml), ether (50 ml) in that order. The solid was vacuum dried to get 0.5 g (83%) of title compound.

EXAMPLE 24

[Ethoxy-(4-phenylbutyl)phosphinyl]acetic acid, ethyl ester

To a solution of 4-phenylbutyl phosphonous acid, ethyl ester (0.5 g, 0.0022 mole) in chloroform (10 ml) was added triethylamine (0.34 ml, 0.0024 mole) and the solution was cooled in an ice bath to 0° C. Trimethyl silyl chloride (0.31 ml, 0.0024 mole) was added to the above solution dropwise, followed by ethyl bromoacetate (0.27 ml, 0.0024 mole). The ice bath was removed and the mixture stirred at room temperature for 6 hours and poured into 50% aqueous HCl (30 ml) and crushed ice (20 g). After shaking the mixture in a separatory funnel, the chloroform layer was separated and the aqueous layer extracted with dichloromethane (2×50 ml). The combined organic phase was washed with brine, dried over anhydrous sodium sulfate and the solvents removed on a rotavap. The resulting yellow oil (0.6 g) was vacuum dried to get 0.58 (84%) of title compound. TLC, silica gel, acetone:hexane (1:1), $R_f=0.28$.

EXAMPLE 25

[Ethoxy-(4-phenylbutyl)phosphinyl]propionic acid, ethyl ester

To a solution of 4-phenylbutyl phosphonous acid, ethyl ester (0.5 g, 0.0022 mole) in chloroform (10 ml) was added triethylamine (0.34 ml, 0.0024 mole) and the solution was cooled in an ice bath to 0° C. Trimethyl silyl chloride (0.31 ml, 0.0024 mole) was added to the above solution dropwise, followed by ethyl 2-bromopropionate (0.32 ml, 0.0024 mole). The ice bath was removed and the mixture stirred at room temperature for 6 hours and poured into 5% aqueous HCl (30 ml) and crushed ice (20 g). After shaking the mixture in a separatory funnel, the chloroform layer was separated and the aqueous layer extracted with dichloromethane (2×50 ml). The combined organic phase was washed with brine, dried over anhydrous sodium sulfate and the solvents removed on a rotavapto give a crude thick oil (0.69 g). TLC, silica gel, acetone:hexane (1:1) $R_f=0.28$

EXAMPLE 26

[Ethoxy-(4-phenylbutyl)phosphinyl]acetyl-L-proline

To a solution of 4-phenylbutyl phosphonous acid, ethyl ester (0.24 g, 0.0011 mole) in chloroform (10 ml) was added triethylamine (0.34 ml, 0.002 mole) and the solution was cooled in an ice bath to 0° C. Trimethyl silyl chloride (0.29 ml, 0.0023 mole) was added to the above solution dropwise, followed by benzyl bromoacetyl-L-proline (0.25 g, 0.0011 mole). The ice bath was removed and the mixture stirred at room temperature for 4 hours and poured into 10% aqueous HCl (30 ml) and crushed ice (20 g). After shaking the mixture in a separatory funnel, the chloroform layer was separated and the aqueous layer extracted with dichloromethane (2×50 ml). The combined organic phase was washed with brine, dried over anhydrous sodium sulfate and the solvents removed on a rotavap. The resulting crude thick oil was vacuum dried to get 0.23 g (57%) of title compound, TLC: silica gel, CH$_2$Cl$_2$:MeOH:HOAc shows one main spot at R$_f$=0.23.

It will be appreciated that the silylating agent employed in the previous examples, namely, trimethyl silyl chloride employed with triethylamine as a base, may be substituted with any of the silylating agents mentioned hereinbefore, namely, monosilylacetamide, bissilylacetamide, monosilyltrifluoroacetamide or bissilyltrifluoroacetamide, which silylating agents need not be employed with a separate base.

EXAMPLE 27

1-[3-[Hydroxy-(4-phenylbutyl)phosphinyl]-1-oxopropyl]-L-proline, (2,2-dimethyl-1-oxopropoxy)methyl ester, lithium salt

A.

1-[3-[Hydroxy-(4-phenylbutyl)phosphinyl]-1-oxopropyl]-L-proline, (2,2-dimethyl-1-oxopropoxy)methyl ester A mixture of [hydroxy-(4-phenylbutyl)phosphinyl]-propionic acid (prepared as described in Example 13) (0.75 g, 0.0028 mole), carbonyldiimidazole (CDI) (0.45 g, 1.0 eq) and THF were stirred under argon at 0° C. for 2 hours. NEt$_3$ (0.8 ml, 2.0 eq) and the tosylate salt of proline pivaloxymethyl ester (1.1 g, 1.0 eq) were added and the resulting solution was stirred at room temperature for 16 hours. The THF was stripped and the residue was partitioned between 1N HCl and EtOAc. The organic phase was washed with 5% NaH$_2$PO$_4$ (2 times), brine and dried (MgSO$_4$). The solvent was stripped to obtain a crude oil (1.2 g). The crude oil was chromatographed on silica (70 g) eluting with (CH$_2$Cl$_2$/HOAc/CH$_3$OH, 95:5:5) to give title A compound (1.0 g, 0.0021 mole, 74% yield) as a colorless glass. TLC (95:5:5, CH$_2$Cl$_2$:HOAc:CH$_3$OH) gave one spot, R$_f$=0.35.

B.

1-[3-[Hydroxy-(4-phenylbutyl)phosphinyl]-1-oxopropyl]-L-proline, (2,2-dimethyl-1-oxopropoxy)methyl ester, lithium salt Title A compound (940 mg, 1.95 mmole) was dissolved in acetone. Li$_2$CO$_3$ (73 mg, 0.975 mmole) and water were added to the acetone solution. The heterogeneous mixture became homogeneous after 2½ hours. The acetone and some water was removed and the resulting solution was millipored and lyophilized. A dense white lyophilizate (800 mg, 1.60 mmole, 86% yield) was obtained which is useful as an angiotensin converting enzyme inhibitor in the treatment of hypertension.

Anal. Calcd for C$_{24}$H$_{35}$NO$_7$P.Li.0.5 moles of H$_2$O: N, 2.82: C, 58.06; H, 7.31; P. 6.2; Found: N, 2.76; C, 57.91; H, 7.36; P, 6.2.

EXAMPLE 28

(±)-1-[3-[Hydroxy-(4-phenylbutyl)phosphinyl]-2-methyl-1-oxopropyl]-L-proline, dilithium salt

A.

(±)-1-[3-[Hydroxy-(4-phenylbutyl)phosphinyl]-2-methyl-1-oxopropyl]-L-proline, benzyl ester A mixture of [hydroxy-(4-phenylbutyl)phosphinyl]-1-methylpropionic acid (prepared as described in Example 14) (0.75 g, 0.0026 mole), carbonyldiimidazole (0.42 g, 1.0 eq), and THF was stirred under argon for 1 hour at 0° C. NEt$_3$ (0.72 ml, 2.0 eq) and proline benzyl ester (0.63 g, 1.0 eq) were added and the resulting heterogeneous mixture was stirred at room temperature for 16 hours. The THF was stripped and the residue was partitioned between EtOAc and 1N HCl. The organic portion was washed with 5% NaH$_2$PO$_4$ (3 times), brine, dried (MgSO$_4$), and evaporated. The crude product (1.05 g) was chromatographed on silica (75 g) eluting with CH$_2$Cl$_2$/HOAc/CH$_3$OH (95/5/5) to give title compound (1.0 g, 0.0021 mole, 82% yield) as a colorless glass. TLC (95/5/5, CH$_2$Cl$_2$/HOAc/CH$_3$OH) major spot R$_f$=0.33.

B.

(±)-1-[3-[Hydroxy-(4-phenylbutyl)phosphinyl]-2-methyl-1-oxopropyl]-L-proline

Benzyl ester from Part A (1.0 g, 0.0021 mole) in CH$_3$OH (50 ml) was treated with 10% Pd/C (100 mg) and shaken on a Parr hydrogenation apparatus for 3 hours at 35 psi. The reaction mixture was filtered through a Celite bed, washing several times with CH$_3$OH. The CH$_3$OH was stripped to give title B diacid (0.8 g, 0.0021 mole, quantitative). TLC (butanol/H$_2$O/HOAc, 4/1/1) one spot R$_f$=0.47.

C.

(±)-1-[3-[Hydroxy-(4-phenylbutyl)phosphinyl]-2-methyl-1-oxopropyl]-L-proline, dilithium salt Title B diacid (0.80 g, 0.021 mole) was dissolved in water and 1N LiOH (2.0 ml, 1.0 eq) and run on AG40W-X8 (Li+) resin (40 ml). The aqueous solution was millipored and lyophilized. A very dense lyophilizate (0.75 g, 0.0017 mole, 91% yield) was obtained of the above title which is useful as an angiotensin-converting enzyme inhibitor in the treatment of hypertension.

Anal. Calcd for C$_{19}$H$_{26}$NO$_5$PLi$_2$ 3.5 moles of H$_2$O: C, 50.00; H, 7.29; N, 3.07; P, 6.8; Found: C, 50.05; H, 6.92; N, 3.04; P, 6.8.

What is claimed is:

1. A method for preparing a phosphinic acid intermediate of the structure $$R^1 - \underset{\underset{OR}{|}}{\overset{\overset{O}{\|}}{P}} - (CH_2)_n - \underset{\underset{}{|}}{\overset{\overset{R^2}{|}}{C}}H - Z$$

wherein

R is H or lower alkyl;

R$^1$ is lower alkyl, aryl, arylalkyl, cycloalkyl, or cycloalkylalkyl;

R$^2$ is H or lower alkyl;

Z is H, lower alkyl,

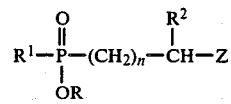

—(CH$_2$)$_4$C$_6$H$_5$, —CO$_2$R$^3$ (wherein R$^3$ is H or lower alkyl),

(wherein R$^4$ is H, lower alkyl, aryl or arylalkyl), —CN, or

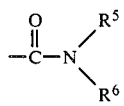

wherein $R^5$ and $R^6$ may be the same or different and are selected from the group consisting of H, lower alkyl, aryl, aryl-lower alkyl, cycloalkyl or cycloalkylalkyl and at least one of $R^5$ and $R^6$ is other than H, or $R^5$ and $R^6$ can be taken with the N-atom to form a 5-, 6- or 7-membered heterocyclic ring which 5-, 6- or 7-membered N-containing ring may or may not contain a $CO_2R^3$ group and which 5- or 6-membered N-containing ring may or may not be fused to an aryl ring; and n is 0 or 1, which comprises reacting a phosphonous acid or ester thereof of the structure

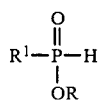

wherein R and $R^1$ are as defined above with an alkylating agent of the structure

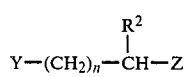

wherein Y is a leaving group, and $R^2$, n and z are as defined above, employing a molar ratio of phosphonous acid or ester thereof to the alkylating agent of within the range of from about 0.5:1 to about 10:1, in the presence of a silylating agent, employing a molar ratio of phosphonous acid or ester to silylating agent of within the range of from about 0.06:1 to about 2:1, and in the presence of an inert organic solvent to form the phosphinic acid intermediate and separating the phosphinic acid intermediate from the reaction mixture.

2. The method as defined in claim 1 wherein n is 0 and $R^2$ is H.

3. The method as defined in claim 1 wherein the reaction is carried out in the presence of a base which is triethylamine, pyridine or N,N-dimethylamine.

4. The method as defined in claim 1 wherein the inert organic solvent is chloroform, acetonitrile, dichloromethane, dichloroethane, ethyl ether, tetrahydrofuran or dioxane.

5. The method as defined in claim 1 wherein the silylating agent is trimethyl silylchloride and triethylamine, monosilylacetamide, bissilylacetamide, monosilyltrifluoroacetamide or bissilyltrifluoroacetamide, or trimethylsilyl imidazole.

6. The method as defined in claim 1 wherein the silylating agent is trimethyl silylchloride and triethylamine.

7. The method as defined in claim 1 wherein in the phosphonous acid or ester, R is lower alkyl, and in the alkylating agent Z is an ester, lower alkyl,

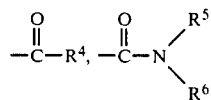

or CN.

8. The method as defined in claim 7 wherein the phosphonous acid or ester is employed in a molar ratio to the alkylating agent of within the range of from about 0.5:1 to about 10:1, and the phosphonous acid or ester is employed in a molar ratio to the silylating agent of within the range of from about 0.1:1 to about 2:1.

9. The method as defined in claim 1 wherein in the phosphonous acid or ester, R is H and in the alkylating agent Z is an ester, lower alkyl,

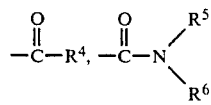

or CN.

10. The method as defined in claim 9 wherein the phosphonous acid is employed in a molar ratio to the alkylating agent of within the range of from about 0.5:1 to about 10:1, and the phosphonous acid is employed in a molar ratio to the silylating agent of within the range of from about 0.1:1 to about 1:1.

11. The method as defined in claim 1 wherein in the phosphonous acid or ester, R is lower alkyl, and in the alkylating agent Z is COOH or

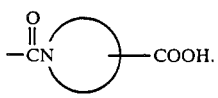

12. The method as defined in claim 11 wherein the phosphonous acid ester is employed in a molar ratio to the alkylating agent of within the range of from about 0.5:1 to about 10:1, and the phosphonous acid ester is employed in a molar ratio to the silylating agent of within the range of from about 0.06:1 to about 1:1.

13. The method as defined in claim 1 wherein in the phosphonous acid or ester, R is H, and in the alkylating agent Z is COOH or

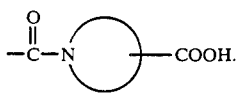

14. The method as defined in claim 1 wherein Y is a halogen group, mesyl or tosyl.

15. The method as defined in claim 13 wherein the phosphonous acid is employed in a molar ratio to the alkylating agent of within the range of from about 0.5:1 to about 10:1, and the phosphonous acid is employed in a molar ratio to the silylating agent of within the range of from about 0.06:1 to about 1:1.

16. The method as defined in claim 1 wherein the reaction between the phosphonous acid or ester and the silylating agent is carried out at a temperature of within the range of from $-10°$ C. to refluxing temperature.

17. The method as defined in claim 1 wherein the phosphonous acid is
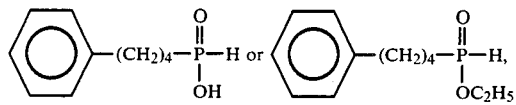
the alkylating agent is $BrCH_2CO_2CH_2C_6H_5$, $BrCH_2CO_2H$, $BrCH_2CO_2CH_2CH_3$,
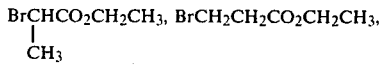
and the silylating agent is $(CH_3)_3SiCl$ and $(C_2H_5)_3N$ or monotrimethylsilylacetamide.
* * * * *